United States Patent [19]
Sanso

[11] Patent Number: 5,048,515
[45] Date of Patent: Sep. 17, 1991

[54] RESPIRATORY GAS SUPPLY APPARATUS AND METHOD

[76] Inventor: David W. Sanso, 701 Harlan-E38, Lakewood, Colo. 80214

[21] Appl. No.: 271,525

[22] Filed: Nov. 15, 1988

[51] Int. Cl.$^5$ ............................................. A61M 16/00
[52] U.S. Cl. ........................... 128/204.26; 128/204.21; 128/204.18
[58] Field of Search .................... 128/204.18, 204.21, 128/204.23, 204.26

[56] References Cited

U.S. PATENT DOCUMENTS

| | | | |
|---|---|---|---|
| 3,768,468 | 10/1973 | Cox | 128/204.21 |
| 3,923,056 | 12/1975 | Bingmann et al. | 128/204.21 |
| 3,961,627 | 6/1976 | Ernst et al. | 128/204.21 |
| 3,972,327 | 8/1976 | Ernst et al. | 128/204.21 |
| 3,976,064 | 8/1976 | Wood et al. | 128/204.21 |
| 3,976,065 | 8/1976 | Durkan | 128/204.24 |
| 4,036,221 | 7/1977 | Hillsman et al. | 128/204.23 |
| 4,206,754 | 6/1980 | Cox et al. | 128/204.26 |
| 4,211,221 | 7/1980 | Schwanbom et al. | 128/204.26 |
| 4,414,982 | 11/1983 | Durkan | 128/716 |
| 4,457,303 | 7/1984 | Durkan | 128/204.24 |
| 4,461,293 | 7/1984 | Chen | 128/204.23 |
| 4,462,398 | 7/1984 | Durkan et al. | 128/200.14 |
| 4,484,578 | 11/1984 | Durkan et al. | 128/204.24 |
| 4,506,666 | 3/1985 | Durkan | 128/204.23 |
| 4,519,387 | 5/1985 | Durkan | 128/204.23 |
| 4,570,631 | 2/1986 | Durkan | 128/204.23 |
| 4,635,631 | 1/1987 | Izumi | 128/204.23 |
| 4,677,975 | 7/1987 | Edgar et al. | 128/204.23 |
| 4,681,099 | 7/1987 | Sato et al. | 128/204.23 |

Primary Examiner—Aaron J. Lewis
Attorney, Agent, or Firm—J. Preston Oxenham

[57] ABSTRACT

A supplemental respiratory gas supply control apparatus and method for providing supplemental gas to an in vivo respiratory system includes a pressure sensor adapted to produce pressure indicative signals indicative of pressures sensed, a gas flow control valve, a sensor communication control valve, and a central control unit adapted to receive pressure indicative signals generated by the pressure sensor and to control the gas control valve and the sensor communication control valve in accordance with the signals received. The gas control valve is connected to a source of supplemental gas at regulated pressure and has two positions, a first position isolating the source of supplemental gas from the single hose cannula and a second position communicating the source of supplementary gas with the cannula hose to provide a flow of supplementary gas to the in vivo respiratory system. The pressure sensor communication control valve has a first mode placing the pressure sensor in communication with the cannula hose to allow the pressure sensor to sense the pressure within the hose and a second mode in which the pressure sensor is placed in communication with the ambient atmosphere. The central control unit initially places the gas control valve in the first position and the sensor communication valve in the first mode to monitor the pressure within the cannula hose.

34 Claims, 3 Drawing Sheets

RESPIRATORY GAS SUPPLY APPARATUS AND METHOD

TECHNICAL FIELD

The present invention relates generally to systems for providing supplemental respiratory gas to in vivo respiratory systems and, more particularly, to a method and apparatus for providing supplemental oxygen to assist the respiratory function of patients. Most particularly, the present invention relates to a method and apparatus for providing supplemental oxygen, on demand, through a single hose cannula to aid respiration by the in vivo respiratory system of a patient.

BACKGROUND OF THE INVENTION

The basic prior art systems for providing supplemental respiratory gases have consisted of a source of supplemental gas at a regulated pressure which is connected to a cannula hose with outlets for dispelling the supplemental gas in one or both nares of a patient's nose. These systems deliver oxygen at a constant rate without regard to the patient's respiratory cycle. Thus, a flow of oxygen is provided constantly by these systems, not only during the inhalation portion of the respiratory cycle characterized by negative pressure at the nares and the drawing in of respiratory gases, but also during the exhalation portion of the cycle characterized by positive pressure at the nares and the expelling of gas from the in vivo respiratory system. This approach not only wastes supplemental gas which is vented to the ambient atmosphere during exhalation, but further, where the supplemental gas is oxygen, may create an oxygen enriched atmosphere about the patient's face which creates a danger of fire related injury. These problems related to continuous supplemental gas supply systems are aggravated by the fact that the exhalation portion of an in vivo system's respiratory cycle is commonly of a longer duration than the inhalation portion of the cycle, thus wasting a larger portion of the supplemental gas.

Demand systems are known in the prior art which utilize a dual hose cannula and pressure sensing device to provide supplemental gas only during the inhalation portion of the respiratory cycle characterized by negative pressure at the nares, or point of inhalation by the in vivo system. Typically, in such systems, a first hose of the two hose cannula is dedicated to communicate a pressure sensor with a nare so that the sensor may sense positive and negative pressures at the point of inhalation which are associated with the respiratory cycle. The pressure sensor is then used to control the flow of supplemental gas from a constant pressure gas source into the second hose of the cannula and on to the second nare to provid a flow of supplemental gas only during periods of negative pressure characterizing the inhalation portion of the respiratory cycle. While such systems may be effective in reducing waste of the supplemental gas and reducing oxygen concentrations in the local atmosphere, double hose cannulas are cumbersome and expensive in comparison to the single hose variety, thus increasing the expense and reducing the utility of such systems.

Other demand systems of the prior art have attempted to utilize a single hose cannula to both communicate a pressure sensing device with a nare at the point of inhalation of the in vivo respiratory system and to provide supplemental gas to the in vivo system. Generally, in these systems, the pressure sensing device is first connected to the cannula to monitor pressure within the hose. Upon detection of a negative pressure conveyed through the cannula hose to the pressure sensor, indicating the initiation of inhalation at the beginning of a respiratory cycle, supplemental oxygen under pressure is introduced into the cannula for a predetermined period of time. In these systems, the time interval over which supplemental gas is provided during each respiratory cycle must be pre-determined, and cannot be controlled by the occurrence of positive pressure characteristic of the exhalation portion of the respiratory cycle. This is because the residual local high pressure of the supplemental gas introduced into the cannula hose, which results from the pressure gradient along the length of the hose associated with the flow of supplemental gas to the nare, masks the cycle indicative pressures which would otherwise propagate through the cannula hose from the nare. Thus, in single hose systems, the length of the oxygen supply interval is typically set manually at a constant value.

Alternatively, in these systems, supplemental gas is not introduced during selected respiratory cycles so that cycle indicative pressures in the cannula hose can be monitored and the duration of the inhalation portion of a sample cycle determined. The duration of the sample cycle is then utilized as a basis for setting the duration of one or more subsequent supplemental gas supply intervals. Concomitant with this latter approach is a reduction in overall supply of oxygen which, in turn, generally results in a lower concentration of supplemental gas in the blood stream of the patient than would result from supplying supplemental gas during the inhalation portion of every respiratory cycle.

Further problems occur in these prior art single hose cannula systems due to their valving and switching arrangements. Typically, the single hose prior art devices utilize a two-position three-port valve with a first port connected with the interior of the cannula hose and the second and third ports connected to the supplemental gas supply and the pressure sensor, respectively. In one position, the valve will connect the first port with the second port and in an alternative position, the valve will connect the first port with the third port. A control device switches the valve between these two positions so that, at any time, either the pressure sensor or the supplemental gas supply is in communication with the cannula hose. Difficulties with such systems arise where pressure transducers or piezo-electric pressure detection devices are utilized to measure pressures within the cannula hose because, when the position of the three-port valve is changed from the gas supply position to the pressure sensing position, a high residual pressure is present at the location of the first port in the cannula hose for a time after the switch due to the pressure gradient along the hose associated with the flow of supplemental gas to the point of gas introductin at the nare. These high pressures often cause the calibration point of pressure sensors to drift excessively and may damage the pressure sensors.

DISCLOSURE OF THE INVENTION

It is an object of the present invention to provide a single-hose cannula supplemental respiratory gas supply system for an in vivo respiratory system.

It is a further object to provide a single-hose supplemental respiratory gas supply system which can provide supplemental gas for only an appropriate duration during each respiratory cycle coinciding with the inhalation portion of the particular respiratory cycle. Thus, it is an object of the present invention to determine, at the beginning of each individual respiratory cycle, the appropriate period over which to supply supplemental gas duriing that respiratory cycle.

Yet another object of the present invention is to provide a single-hose cannula supplemental respiratory gas supply system which utilizes a pressure sensing device to detect the initiation of each respiratory cycle to initiate administration of a supplemental gas, yet does not allow the pressure sensing device to be subject to high residual supplemental gas pressures within the cannula hose.

Still further, it is an object of the present invention to provide a supplemental respiratory gas supply system which will calibrate to ambient atmospheric pressure at the beginning of each operational period to compensate for effects of changes in mechanical and electrical components of the system over time.

It is another object of the present invention to provide a supplemental respiratory gas supply system which will sound an alarm upon the occurrence of an apneic event.

Still further, it is an object of the present invention to provide a supplemental gas supply system which will continue to provide supplemental gas to the in vivo system during power or control system failure.

In accordance with these objectives, the supplemental respiratory gas supply apparatus and method of the present invention utilizes a control unit responsive to pressure indicative signals from a pressure sensing device to control two independent valve units to provide supplemental gas to an in vivo respiratory system through a single-hose cannula. A gas valve unit controls the flow of supplemental gas from a supplemental gas source at regulated pressure to the single-hose cannula and a sensor valve unit selectively communicates the pressure sensing device with the interior of the single hose of the cannula or with the ambient atmosphere.

A supply of supplemental gas, preferably at a constant regulated pressure greater than atmospheric pressure, is connected to the gas valve unit which is, in turn, connected with the cannula hose. When in a first position, the gas valve unit blocks off and isolates the supplemental gas supply source. When switched to a second position, the gas valve unit places the constant pressure supplemental gas source in communication with the cannula hose to provide a flow of gas through the cannula hose to the in vivo respiratory system.

The pressure sensing device is connected to the sensor valve unit which has two alternative modes. When in the first mode, the sensor valve unit communicates the pressure sensing device with the cannula hose to allow the sensing device to sense the pressure within the hose. In the second mode, the sensor valve unit communicates the pressure sensing device with the ambient atmosphere so the pressure sensed by the sensing device is ambient atmospheric pressure, or zero gauge pressure.

The gas valve unit is structured in such a manner that, when no power is available to the unit, it will be at repose in the second position. Thus, in the case of a power failure, so long as supplemental gas under pressure is provided to the gas valve unit, supplemental gas will be provided continuously through the cannula hose to the in vivo system.

When operation of the supplemental respiratory gas supply system is initiated, and power is provided to the system, the gas valve unit remains in the second position and the sensor valve is placed in the second mode, placing the pressure sensor in communication with the atmosphere. Upon startup, the control unit monitors the pressure indicative signal of the pressure sensing device to calibrate the system to a threshold pressure indicative signal at atmospheric, or zero gauge, pressure. Once calibration is completed, the gas valve unit is switched to the first position and the sensor valve unit is switched to the first mode, placing the pressure sensing device in communication with the interior of the cannula hose. The control unit then continues to monitor the pressure indicative signal to determine the pressure, relative to the threshold pressure, within the cannula hose.

Upon occurrence of a negative pressure indicative signal indicative of a pressure less than atmospheric pressure, the control unit initiates a time delayed switch of the sensor valve from the first mode to the second mode while continuing to monitor the negative pressure indicative signal characteristic of inhalation at the beginning of the respiratory cycle. After a predetermined pressure-peak-determination time interval, the pressure sensor is switched to atmospheric pressure.

After a supplemental-gas-administration-delay interval, following the time the sensor valve is switched from the first to the second mode, the gas valve is switched from the first position to the second position to connect the supplemental gas source to the cannula hose and begin an interval of supplemental gas administration.

The duration of the supplemental gas administration interval over which supplemental gas is supplied to the in vivo system is determined by the control unit based upon the absolute magnitude of the greatest negative pressure indicated during the pressure-peak-determination interval. Generally, the more negative the peak pressure during the interval, the longer the duration of the supplemental-gas-administration interval. At the end of the supplemental gas administration interval, the control unit switches the gas valve back to the first position to shut off the supply of gas and isolate the cannula hose from the supplemental gas source.

After isolating the gas supply, the control unit delays switching the sensor valve from the first to the second mode until the expiration of a sensor-connection-delay interval. This sensor-connection-delay interval, while inconsequential relative to the duration of the inhalation or exhalation portions of the respiratory cycle, is of sufficient duration to provide adequate time for the pressure differential between the portion of the cannula hose which is in periodic communication with the supplemental gas supply source and the pressure at the point of introduction of gas to the in vivo system to become very small due to the decrease in pressure gradient over the length of the cannula hose resulting from diminishing supplemental gas flow over the delay period. The sensor-connection-delay interval, together with the supplemental-gas-administration-delay interval, assures the pressure sensing device will not be subject to pressures within the cannula hose sufficiently high to cause excessive calibration drift or damage the pressure sensing device.

From the above description, it will be evident that the method by which the respiratory gas supply control apparatus of the present invention provides supplemental respiratory gas in response to demands of the in vivo system includes connecting the pressure sensing device to the cannula hose to continuously measure the pressure within the cannula hose; monitoring the pressure within the cannula hose until the time of an initial occurrence of a pressure less than atmospheric pressure; waiting a predetermined period of time after the time of initial occurrence of a pressure less than atmospheric pressure; recording the peak negative pressure which occurs within the cannula hose during that period of time; disconnecting the pressure sensing device from the cannula hose; waiting a predetermined time after disconnecting the pressure sensing device; connecting a source of supplemental gas to the cannula hose to begin a period of supplemental gas administration; continuing to provide supplemental gas to the in vivo system for a time interval based upon the absolute magnitude of the peak negative pressure recorded; at the end of the supplemental gas administration interval, disconnecting the source of supplemental gas from the cannula hose; waiting a predetermined period of time after disconnecting the source of supplemental gas from the cannula hose; reconnecting the pressure sensing device to the cannula hose and again continuously monitoring the pressure within the cannula hose to successively repeat the foregoing steps to provide supplemental gas to the in vivo respiratory system on a continuing basis.

The control unit of the present invention further includes a timing device to time the interval between successive supplemental gas supply cycles. Should that time exceed a predetermined time, an apneic event alarm is sounded.

Other objects, advantages and aspects of the invention will become apparent upon reading of the following detailed description and claims and upon reference to the accompanying drawings.

DETAILED DESCRIPTION OF THE INVENTION

Figure 1:
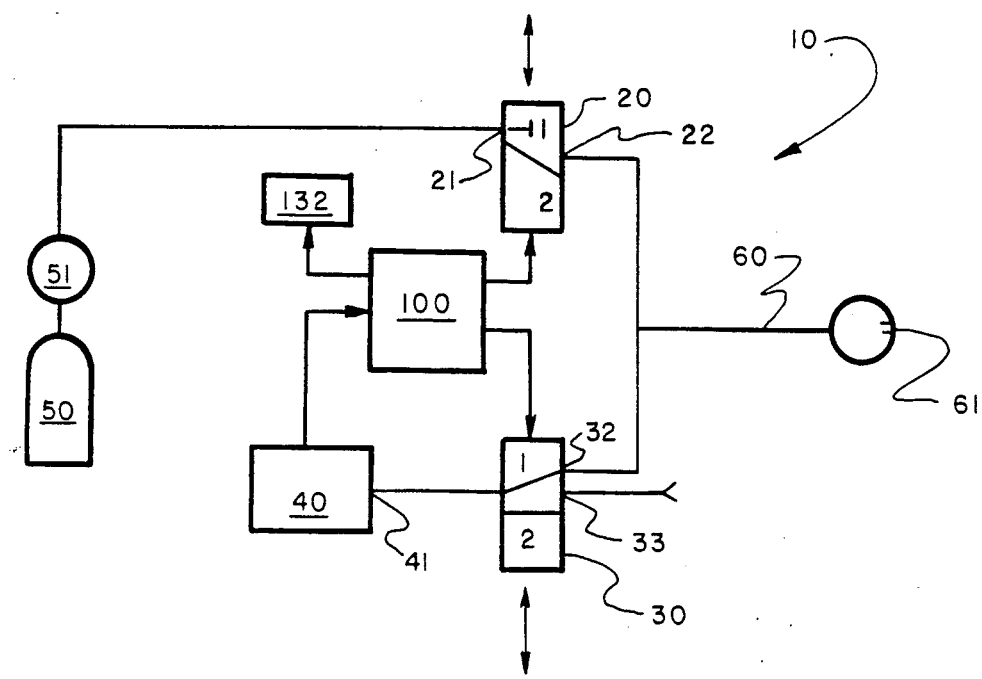
FIG. 1 is a block diagram of a supplemental respiratory gas supply apparatus embodying the present invention.

FIG. 1 is a simplified block illustration of a supplemental respiratory gas supply control apparatus 10 including an embodiment of the present invention. Supplemental respiratory gas supply control apparatus 10 comprises gas valve unit 20, sensor valve unit 30, pressure sensing device 40 and control unit 100.

Gas valve unit 20 controls the flow of supplemental respiratory gas at constant pressure to cannula hose 60. Supplemental respiratory gas, for example, oxygen, from source 50 is provided at constant pressure to input port 21 of gas valve unit 20 by pressure regulator 51. Gas valve unit 20 is responsive to a control signal generated by control unit 100 to switch between two positions. When in the first position, gas valve unit 20 seals off the supplemental gas supply and isolates it from the cannula hose 60. When in the second position, gas valve unit 20 places gas valve unit input port 21 in communication with gas valve unit output port 22 to allow supplementary gas at a constant pressure of, for example, 22 psi, from pressure regulator 51 to flow into cannula hose 60 to supply supplemental gas through the cannula hose to the point of inhalation of the in vivo respiratory system at 61.

Sensor valve unit 30 provides alternative communication between pressure sensor 40 and the interior of the cannula hose 60 or between pressure sensor 40 and ambient atmospheric pressure. Pressure sensor port 31 of sensor valve unit 30 is connected to pressure sensing port 41 of pressure sensor 40, while cannula port 32 of sensor valve unit 30 is in communication with the interior of cannula hose 60 and atmospheric pressure port 33 of sensor unit 30 is open to ambient atmospheric pressure. Sensor valve unit 30 is responsive to control signals generated by control unit 100 to switch between two modes. When sensor valve unit 30 is in the first mode, pressure port 31 is placed in communication with cannula port 32, the pressure sensing port 41 of pressure sensor 40 is in communication with the interior of cannula hose 60, and, thus, pressure sensor 40 will sense pressure within the cannula hose 60. When sensor valve unit 30 is in the second mode, pressure sensor port 31 is placed in communication with atmospheric pressure port 38 and pressure sensor 40 will sense ambient atmospheric, or zero gauge, pressure. Valve units 20 and 30 are preferably fast-acting, energy efficient valve mechanisms and may be, for example, solenoid activated poppet valves.

Pressure sensor 40 may be any of the many well-known pressure sensing devices of the art capable of producing a pressure indicative signal indicative of the pressure at a pressure sensing port and may be, by way of example, a pressure transducer or piezo-electric device. Control unit 100 of the exemplary supplemental respiratory gas supply apparatus 10 of FIG. 1 is adapted to receive the pressure indicative signals of pressure sensor 40 and to control the position of the gas valve unit 20 and the mode of the sensor valve unit 30 in a programmed manner in accordance with the pressure indicative signals received from pressure sensor 40.

Gas valve unit 20 is configured in such a manner that, when no power is provided to the supplemental respiratory gas supply system, gas valve unit 20 will be in repose in the second position. This power off configuration of valve unit 20 assures that, should there be a power failure, supplemental respiratory gas will be provided to the in vivo respiratory system through the cannula hose 60 on a continuous basis so long as supplemental gas at constant pressure is provided to the input port 21 of gas valve unit 20.

When operation of the supplemental respiratory gas supply unit is initiated, and power is provided to the control unit, gas valve unit 20 remains in the second position, while sensor valve unit 30 is switched to its second mode placing pressure sensing port 41 of pressure sensor 40 in communication with the ambient atmosphere. Thus, pressure sensor 40 will generate a pressure indicative signal indicative of ambient atmospheric, or zero gauge, pressure. Control unit 100 then calibrates to this pressure indicative signal of pressure sensor 40 indicative of the threshold pressure.

Once control unit 100 has calibrated to the threshold signal, control unit 100 switches the gas valve 20 from the second to the first position to isolate the supplemental gas source from the cannula and, after a time delay as explained below, switches sensor valve 30 from the second mode to the first mode placing pressure port 41 of sensor 40 in communication with the interior of cannula hose 60. Control unit 100 then monitors the pressure indicative signals of pressure sensor 40. With gas valve unit 20 in the first position, isolating the supplementary gas source at constant pressure from cannula hose 60, pressures within the cannula hose will be determined by propagation of pressures from the point of interface between the in vivo respiratory system with cannula hose, 61, to the point of communication with pressure sensor 40. Thus, pressure sensor 40 will produce a pressure indicative signal characteristic of the respiratory cycle of the in vivo respiratory ststem.

Figure 2:
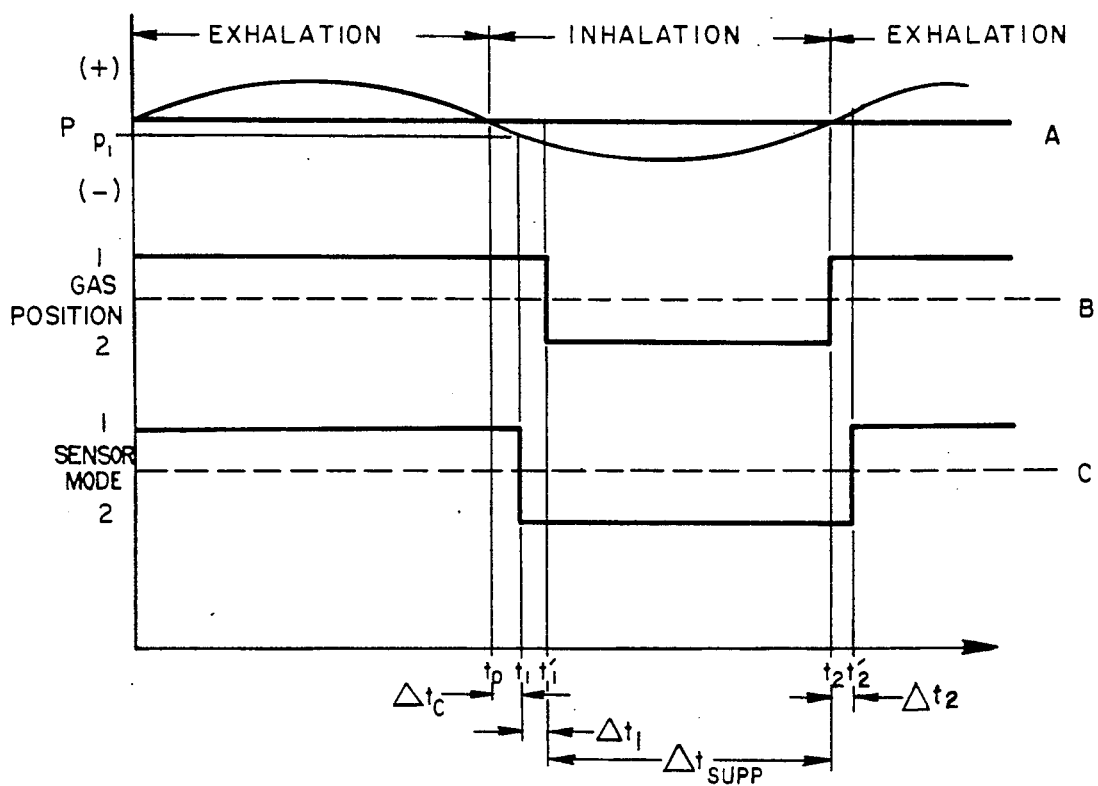
FIG. 2 is a graphic representation of the relationship between the switching of the position of the gas valve and the switching of the mode of the sensor valve, represented by graphs B and C, respectively, relative to pressure occurrences in the cannula hose characteristic of the in vivo respiratory cycle, represented by graph A.

In response to the pressure indicative signals received from pressure sensor 40, control unit 100 controls gas valve unit 20 and sensor valve unit 30 in a programmed manner as graphically represented in FIG. 2. In that illustration, the top graph, A, represents the respiratory cycle of the in vivo respiratory system as characterized by the variation in pressure, relative to atmospheric pressure, over time corresponding to inhalation and exhalation at interface point 61 with the cannula hose 60. The characterizing pressure pattern propagates down the cannula hose 60 to the point of communication with the cannula port 32 of the sensor valve unit 30 to the pressure sensing port 41 of the pressure sensor unit 40 when the sensor valve unit 30 is in the first mode. Pressures represented above the baseline in graph A are pressures greater than atmospheric pressure and are indicative of the exhalation portion of a respiratory cycle. Pressures below the baseline are negative pressures and are indicative of the inhalation portion of respiratory cycles. Thus, the points at which the line representing pressure crosses from above to below the line, indicating a change from positive to negative pressure, at time $t_0$, are indicative of the beginning of inhalation and the initiation of a respiratory cycle. In FIG. 2, graphs B and C represent the position of the gas valve unit 20 and the mode of the sensor valve unit 30, respectively, as determined by control unit 100 in response to the pressure pattern of graph A associated with the in vivo respiratory cycle.

Upon receiving a pressure indicative signal indicative of a pressure less than atmospheric pressure, at time $t_0$, control unit 100 initiates a time delayed switching of the sensor valve unit 30 from the first mode to the second mode. Control unit 100 continues to monitor the increasing negative pressure over a set predetermined peak-pressure-determination interval, $\Delta t_c$, until time $t_1$, at which time, as illustrated by graph C of FIG. 2, control unit 100 generates a signal to switch sensor valve unit 30 from the first mode to the second mode, disconnecting pressure sensing port 41 of pressure sensor 40 from the cannula hose and communicating pressure sensor port 41 with atmospheric pressure port 33 at atmospheric pressure. At a time $t_1'$, after delaying a predetermined supplemental-gas-administration-delay interval $\Delta t_1$ from the time of switching sensor valve unit 30 from the first mode to the second mode, $t_1$, control unit 100 generates a signal to switch gas valve unit 20 from the first position to the second position to allow supplemental respiratory gas to flow into the cannula hose and begin a supplemental gas administration interval, as indicated in FIG. 2C.

The duration, $\Delta t_{sup}$, of the supplemental gas administration interval is determined by control unit 100 in accordance with a predetermined relationship to the absolute magnitude of the peak negative pressure, $P_1$, indicated by the presssure indicative signal of pressure sensor 40 during the peak-pressure-determination interval $\Delta t_c$. Due to the short duration of the peak-pressure-determination interval, this will most commonly be the pressure that occurs at the time sensor valve unit 20 is switched from the first to the second mode, $t_1$. The relationsip between the supplemental gas administration period $\Delta t_{sup}$ and the peak pressure $P_1$ may be, for example, a linear relationship of the nature $\Delta t_{sup} = \alpha P_1$, where $\alpha$ is a mathematical constant, or may be any other functional relationship determining $\Delta t_{sup}$ dependent upon the pressure $P_1$.

At the end of the supplemental gas administration interval, at a time $t_2$, control unit 100 switches gas valve unit 20 from the second position back to the first position to isolate the supplemental gas supply and end administration of supplemental gas to the in vivo system. After switching gas valve unit 20 from the second to the first position, control unit 100 delays switching the sensor valve 30 from the second mode to the first mode until a time $t_2'$, a predetermined sensor-connect-delay interval $\Delta t_2$ after time $t_2$. With the pressure sensing port 41 of pressure sensor 40 in communication with the interior of cannula hose 60, a supplemental gas administration cycle will again be initiated upon the occurrence of a negative pressure indicative of the beginning of an vivo respiratory cycle.

The peak-pressure-determination interval, $\Delta t_1$ and sensor-connect-delay interval, $\Delta t_2$, of the control cycle of control unit 100 are each of a brief and inconsequential duration relative to the overall period of the in vivo system's respiratory cycle and are each of a fixed, predetermined duration. Imposition of the supplemental-gas-administration delay interval, $\Delta t_1$, between disconnecting the pressure sensor from the cannula hose and introducing the pressurized supplemental gas into the interior of cannula hose 60 insures the pressure sensor 40 will not be subjected to high pressure within in the cannula hose associated with supplemental gas administration. Imposition of the sensor connection delay interval, $\Delta t_2$, between disconnecting the source of supplemental gas from the cannula hose 60 and placing the pressure sensor 40 in communication with the cannula hose 60 allows the pressure gradient between the point of interface with the in vivo system and the region of the hose near the point of gas introduction and pressure determination to decline sufficiently to assure the pressure at the base of the hose is not sufficient to damage, or aggravate the drift of, pressure sensor 40.

As explained above, the peak negative pressure during the peak-pressure-determinations interval, $P_1$, will most commonly occur at the end of the peak-pressure-determination interval, at time $t_1$. Thus, the peak-pressure-determination interval, $\Delta t_c$, of the control cycle may be considered to provide a fixed base period over which the magnitude of the negative pressure characteristic of the beginning of inhalation increases so that the absolute magnitude of the pressure $P_1$ at the end of that period is indicative of the rate of change of pressure at the time of initiation of inhalation. This rate of change at the beginning of inhalation may in turn be related to the expected duration of the inhalation portion of the respiratory cycle and the expected volume of respiratory gases which will be drawn in by the in vivo respiratory system in the course of the respiratory cycle. Thus, by maintaining the initial interval, $\Delta t_c$, over which the magnitude of the pressure increases constant, the magnitude of $P_1$ itself provides a basis for determination of the appropriate duration of supplemental gas administration at the beginning of the cycle. Those familiar with the art will understand that the rate of change in pressure at the time of negative pressure occurrence might also be determined from pressure history just prior to the occurrence of inhalation or by a digital or analogue differentiating device.

From the above description, it can be seen that the method utilized by control unit 100 of the exemplary embodiment to provide supplemental respiratory gas to an in vivo respiratory system in response to demands by the in vivo system includes first connecting the pressure sensor 40 to the cannula hose 60 to continuously monitor the pressure within the cannula hose. The pressure within the cannula hose is then monitored until the time, $t_0$, of an initial occurrence of a pressure less than atmospheric pressure. After the occurrence of a pressure less than atmospheric pressure, at time $t_0$, control unit 100 waits a predetermined period of time, $\Delta t_c$, after time $t_0$, until a time $t_1$ and, at that time, records the value of the most negative pressure, $P_1$, occurring within the cannula hose during the period of time $\Delta t_c$ and disconnects the pressure sensing device from the cannula hose. Control unit 100 then waits a predetermined period of time $\Delta t_1$, after $t_1$, until a time $t'_1$ and, at that time, connects the source of supplemental gas at predetermined constant pressure to the cannula hose to begin a supplemental gas administration interval of providing supplemental gas to the in vivo respiratory system. Supplemental gas is then provided to the in vivo system for a time interval $\Delta t_{sup}$, the duration of which is dependent uopn the value of $P_1$ in accordance with a predetermined relation. At the end of the time interval $\Delta t_{sup}$, at a time $t_2$, control unit 100 disconnects the source of supplemental gas from the cannula hose to end the supplemental gas administration interval. After disconnecting the source of supplemental gas at time $t_2$, control unit 100 waits a predetermined period of time $\Delta t_2$ until a time $t'_2$, and, then, reconnects the pressure sensor device to the cannula hose to again continuously monitor the pressure within the cannula hose. This process is successively repeated to provide supplemental gas to the in vivo respiratory system on a continuing basis. Those familiar with the art will understand that the time interval of supplementary gas administration, $\Delta t_{sup}$, may be made dependent upon other parameters. For example, the instantaneous rate of change at the time of the initial occurrence of negative pressure at the beginning of an inhalation portion of a respiratory cycle. Also, $\Delta t_{sup}$, might be set at a fixed predetermined interval of time.

Figure 3:
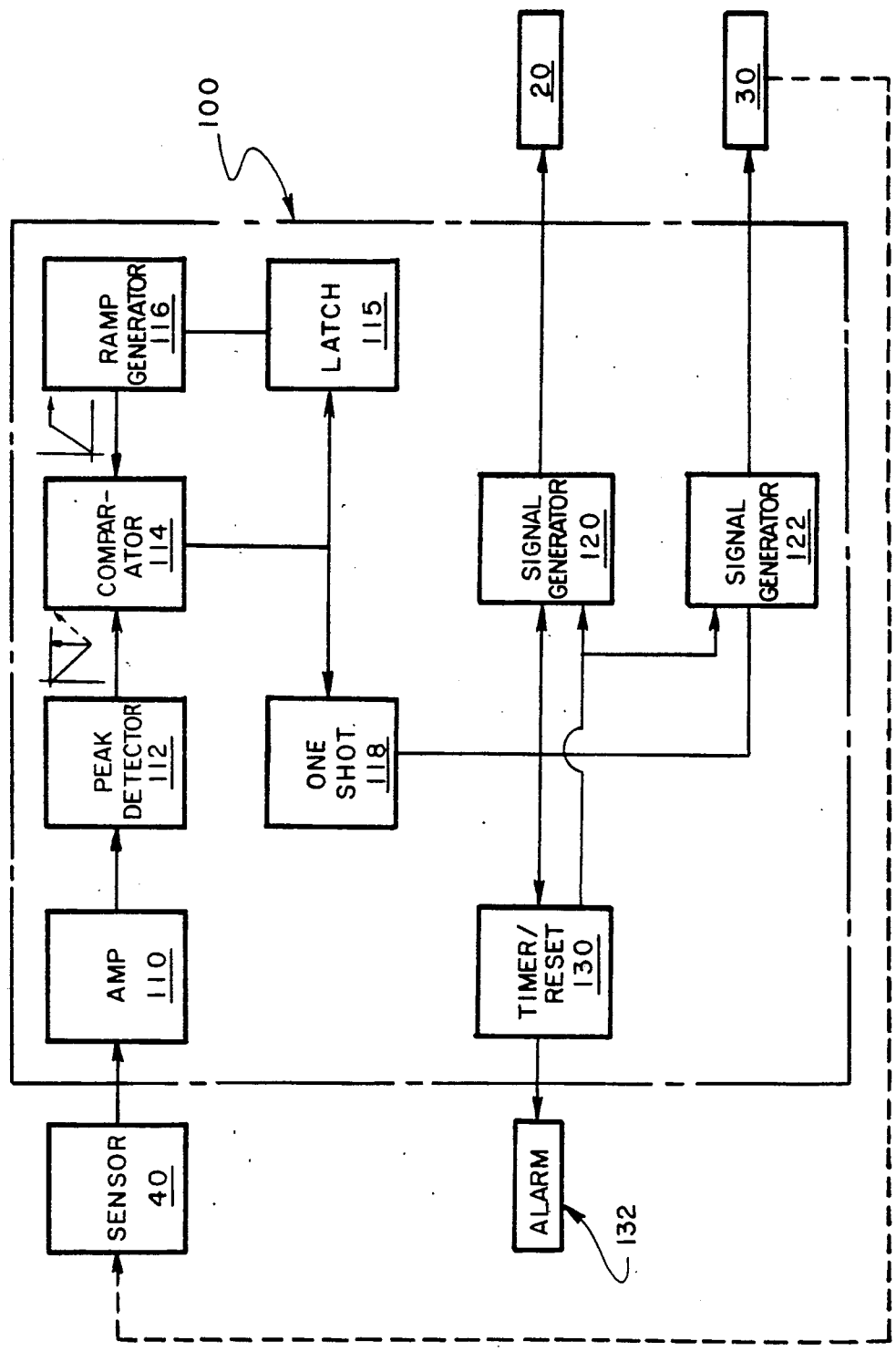
FIG. 3 is a more detailed block diagram including elements of the control unit of a supplemental respiratory gas supply apparatus embodying the present invention.

FIG. 3 is a more detailed block diagram of a preferred embodiment of the supplemental respiratory gas supply apparatus of the present invention showing component elements of the control unit 100. In the preferred embodiment of FIG. 3, gas valve unit 20 is constructed in such a manner that it is in the second position when in repose in the power off state. Pressure sensor 40 is a piezo-electric pressure sensor which generates an electrical voltage signal which is received by control unit 100. In the embodiment of FIG. 3, the pressure indicative signal of sensor 40 is amplified by amplifier 110 before reaching peak detector 112.

Peak detector 112 receives the amplified pressure indicative signal and produces a modified pressure indicative signal which is indicative of a pressure identical to the pressure indicated by the amplified pressure indicative signal except beginning at any time the amplified pressure indicative signal indicates a pressure which is increasing at a rate which exceeds a predetermined maximum rate of increase. Upon such an occurrence, the modified pressure indicative signal will indicate a pressure increasing constantly at a rate corresponding to the predetermined maximum rate until the pressure indicated by the modified signal is again identical to that indicated by the amplified pressure indicative signal. Peak detector 112 will then again produce a modified signal indicative of a pressure identical to the pressure indicated by the amplified signal until the amplified signal again indicates a pressure increasing at a rate in excess of the predetermined maximum rate. During the calibration period, the modified pressure indicative signal produced by peak detector 112 will thus be indicative of a pressure equal to the pressure indicated by the pressure indicative signal of pressure sensor 40.

As described above, when operation of the supplemental respiratory gas supply system of the preferred embodiment of FIG. 3 is initiated and power is first provided to the system, gas valve unit 20 remains in the second position and sensor valve unit 30 is positioned in the first mode. This will place pressure sensing device 40 in communication with the ambient atmosphere and pressure sensor 40 will produce a pressure indicative signal indicative the threshold pressure. A modified signal indicative of the threshold pressure produced by peak detector 112 causes comparator 114 to in turn produce a signal which causes latch 115 to activate ramp generator 116. Ramp generator 116 then produces a trial calibration atmospheric pressure indicative signal indicative of a pressure decreasing linearly with time. When the magnitude of the pressure represented by the trial calibration atmospheric pressure indicative signal generated by the ramp generator 116 matches the magnitude of the pressure represented by modified pressure indicative signal received from the peak detector 112, a signal produced by comparator 114 causes latch 115 to signal ramp generator 116 to cease generating the decreasing pressure signal and to generate a constant calibrated atmospheric pressure indicative threshold signal so long as power is continuously provided to the supplemental respiratory gas supply unit. Thus, the supplemental respiratory gas supply unit is calibrated to ambient atmospheric pressure under the current mechanical and electrical status of pressure sensor 40 and control unit 100.

Once control unit 100 of the exemplary preferred embodiment has calibrated to the threshold pressure as described above, when a modified pressure indicative signal indicative of a pressure less than atmospheric pressure is produced by peak detector 112, that signal will cause comparator 114 to produce a signal indicating inhalation to "one shot" 118. Upon receiving an inhalation signal from comparator 114, one shot 118 produces a cycle signal for a predetermined, minimum set interval of time. Thus, one shot 118 will produce a continuous cycle signal throughout any period of negative pressure indication by the modified pressure indicative signal produced by peak detector 112.

When the cycle signal produced by one shot 118 is received by sensor valve unit signal generator 122, signal generator 122 immediately signals valve 30 to switch from the power on first mode, communicating pressure port 41 of sensor 40 with the interior of cannula hose 60, to the second mode, placing pressure port 41 in communication with ambient atmospheric pressure. In response to the cycle signal, gas valve unit signal generator 120 delays a period of time corresponding to the supplemental-gas-administration-delay interval before signaling gas control valve 20 to switch from the first position to the second position to place the supplemental respiratory gas supply in communication with the interior of cannula 60 to provide supplemental gas to the in vivo respiratory system.

Conversely, when one shot 118 ceases to generate a cycle signal signal generator 120 immediately signals gas valve unit 20 to switch from the second position to the first position to isolate the supplemental respiratory gas source from the cannula. When the cycle signal produced by one shot 118 is no longer received by sensor valve unit signal generator 122, a delay corresponding to the sensor-connect-delay interval, $\Delta t_2$, is provided before control signal generator 122 signals sensor valve unit 30 to switch from the second position to the first position to place pressure port 41 of pressure sensor 40 in communication with the interior of cannula hose 60.

It should be noted that, during the calibration process immediately following the provision of power to the supplementary respiratory gas supply unit, a signal is produced by comparator 114 which, in turn, causes one shot 118 to generate a cycle signal. This in turn causes valve unit 20 to switch to the second position and valve unit 30 to remain in the second mode, to place the supplementary respiratory gas supply unit in a configuration corresponding to the inhalation portion of a respiratory cycle. Thus, the supplemental respiratory gas source will remain in communication with the interior of cannula hose 60 and pressure port 41 of pressure sensor 40 will be vented to ambient atmospheric pressure from the time of initiation of operation until completion of the calibration cycle. Upon completion of the calibration cycle, the signal produced by comparator 114 will cause one shot 118 to cease generating a cycle signal and gas valve 20 and sensor valve 30 to be switched to the pressure monitoring configuration.

In the exemplary preferred embodiment of FIG. 3, when signal generator 122 signals sensor valve 30 to switch from the first to the second mode, a slight delay occurs due to mechanical inertia and electrical impedance of the supplemental respiratory gas supply apparatus. This natural delay period provides a peak-pressure-determination interval during which the negative pressure indicative signal of pressure sensor 40 will reach a peak value. Once the sensor valve unit 30 has switched from the first to the second mode, the pressure indicative signal produced by the pressure sensor 40 will immediately become indicative of atmospheric pressure. When the peak detector 112 receives this signal, indicative of a negative pressure peak followed by a rapid pressure increase, the modified pressure indicative signal produced by peak indicator 112 will be indicative of a pressure increasing only at a limited, constant rate with time until the modified pressure indicative signal generated by the peak detector 112 matches the pressure indicative signal received by peak detector 112. Thus, a modified pressure indicative signal indicative of a pressure less than atmospheric pressure will be produced by peak detector 112 for a period of time which is directly dependent upon the magnitude of the peak negative pressure indicated by the pressure indicative signal of the pressure sensor 40 during the peak-pressure-determination interval. The period of time over which the modified pressure indicative signal indicative of a negative pressure is produced by peak detector 112 will determine the duration of the cycle signal produced by one shot 118 and the supplemental-respiratory-gas-administration interval over which supplemental gas will be provided during the current respiratory cycle of the in vivo respiratory system.

In the exemplary preferred embodiment of FIG. 3, a timer circuit 130 is provided to activate an apneic event alarm 132 should a respiratory cycle of the in vivo respiratory system not occur during a time period longer than a predetermined duration. Timer 130 is configured to receive the cycle control signal generated by one shot 118 and, upon initial receipt of cycle signal, to reset a timing device. Should a period of time greater than a predetermined period of time characteristic of a probable apneic event, for example, a 30 second time period, expire before the timer element is again reset, timer 130 activates alarm 132, which may be, for example, an audible and visual alarm, and causes one shot 118 to produce a ground signal to provide a continuous flow of supplemental respiratory gas to the in vivo system.

Figure 4:
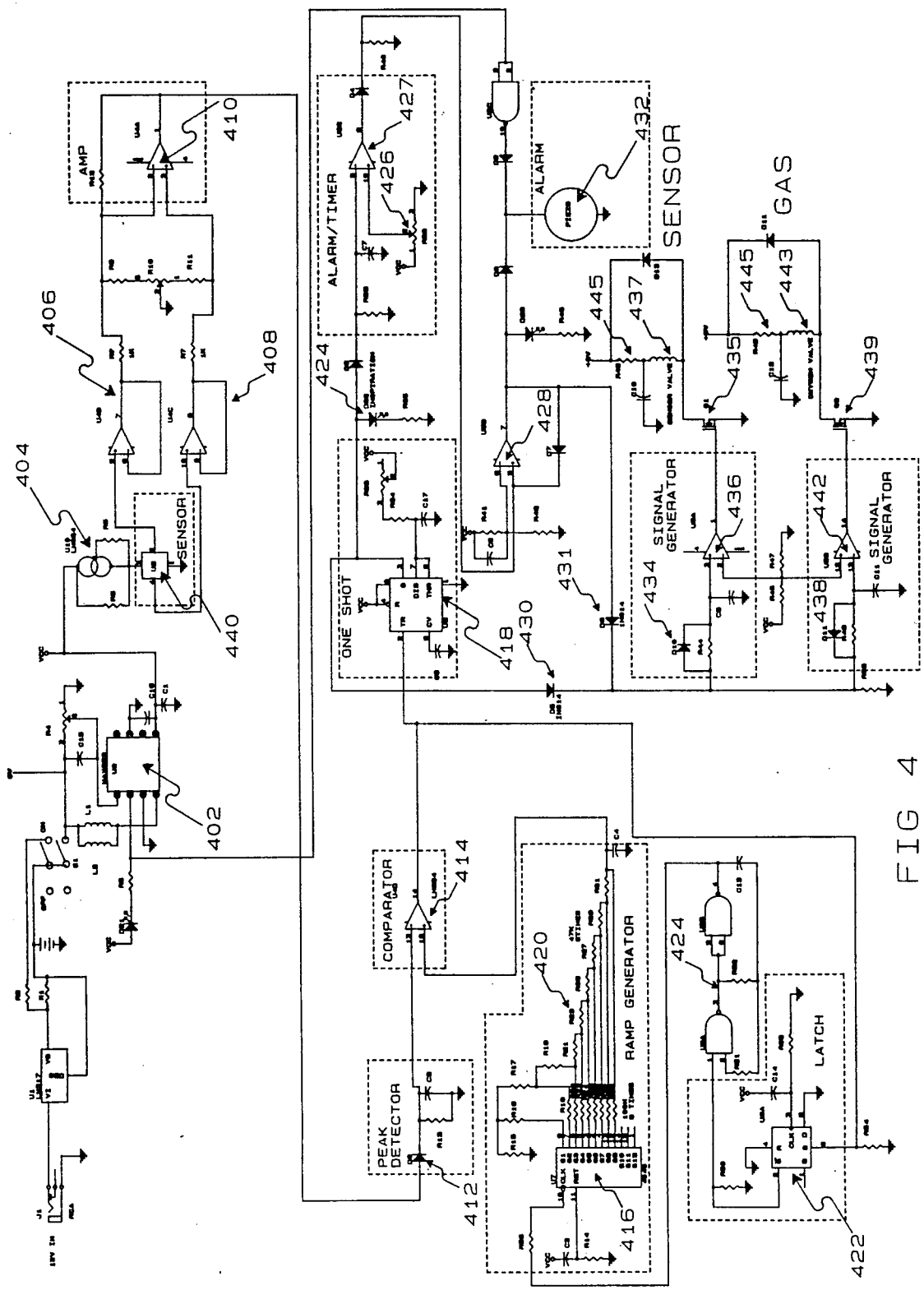
FIG. 4 is a detached schematic diagram of the electrical circuitry of an exemplary preferred embodiment of a supplemental respiratory gas supply apparatus according to the present invention.

FIG. 4 is a detailed schematic drawing showing the electrical circuitry of an exemplary preferred embodiment of a supplemental respiratory gas supply apparatus comprising the present invention. In FIG. 4, portions of the electrical circuitry which correspond to elements of the block diagram of FIG. 3 are identified. The table below gives the resistance in ohms and the capacitance in microfareds of the numbered resistors and capacitors identified by number in FIG. 4.

| COMPONENT TABLE | | | |
|---|---|---|---|
| Resistors (In Ohms) | | | |
| R1–10 | R14–100K | R27–47K | R43–2.3K |
| R2–12 | R15–100K | R28–100K | R44–100K |
| R3–2.2K | R16–100K | R29–47K | R45–33K |
| R4–220K | R17–47K | R30–100K | R46–100K |
| R5–11K | R18–100K | R31–47K | R47–100K |
| R6–39K | R19–47K | R32–100K | R48–100K |
| R7–1K | R20–100K | R34–220K | R49–33K |
| R8–1K | R21–47K | R35–2.2K | R50–100K |
| R9–10K | R22–100K | R36–10M | R51–1M |
| R10–100K | R22–47K | R38–20K | R52–1M |
| R11–10K | R24–100K | R40–100K | R54–100K |
| R12–1.3M | R25–47K | R41–47K | R55–100K |
| R13–1.8M | R26–100K | R42–47K | |
| Capacitors (in microfareds) | | | |
| C1–100 | C5–0.01 | C9–1.5 | C13–0.01 |
| C2–2.2 | C2–1.5 | C10–1000 | C14–4.7 |
| C3–1.5 | C7–4.7 | C11–1.5 | C15–4.7 |
| C4–0.22 | C8–10 | C12–1000 | C16–1 |

In the upper left hand corner of the circuit diagram of the exemplary preferred embodiment, chip 402 is a power supply, such as are well known and available in the industry, which boosts the voltage from a source of power, for example dry cell batteries, the output voltage of which may vary over time, to a constant fixed voltage to power the pressure sensor and control circuit. In the exemplary embodiment of FIG. 4, all points of the circuits are at or above ground when power is provided. Chip 404 is a current source which provides current to the piezio-electric transducer. Chip 404 provides current at appropriate levels to compensate for temperature changes and provide a consistent pressure indicative output from the sensor, for example, when the apparatus is taken from an indoor to an outdoor environment. The piezo-electric pressure transducer 440 provides signals to isolation amplifier circuits 406 and 408. Chip 410 is a portion of the differential amplifier circuit which amplifies the differential signal produced by piezo-electric transducer 440 and isolation amplifiers 406 and 408 to generate a signal to the peak detector. In the exemplary embodiment of FIG. 4, a decrease in pressure sensed by pressure sensor 440 results in an increase in the voltage of the signal generated by amplifier 410. The differential amplifier circuit may amplify the instrumentation circuit output by a factor of, for example, 1.3K.

Diode 412 of the peak detector isolates the control circuit beginning with the peak detector so the modified electrical signal produced by the peak detector circuit flows only toward a first input point of comparator 414. A second input point of comparator 414 is connected to the ramp generator circuit which, together with the latch circuit, provides initial calibration of the control unit to the piezo-electric pressure transducer output, as described in the discussion of FIG. 3 above.

The ramp generator of the exemplary preferred embodiment comprises binary counter 416 which provides a step function input for R-2R circuit 420. R-2R circuit 420 converts an increasing digital output of binary counter 416 to an increasing analog signal which is input to the second input point of comparator 414. Oscillator circuit 424 drives binary counter 416. When the control unit is initially energized, comparator 414 produces a signal at ground. As will be understood from the description to follow, this will energize the sensor valve to place the pressure sensor 440 in communication with the atmosphere until the analog signal produced by the ramp generator circuit exceeds the output of the differential amplifier circuit. At that time, comparator 414 generates a positive signal which causes flip flop 422 to signal oscillator circuit 424 to cease driving binary counter 416 and R-2R circuit 420. This causes the ramp generator circuit to provide a constant threshold output until such time as power is no longer provided to the control unit.

Once calibration is complete, during the inhalation portion of a respiratory cycle, when negative pressure is sensed by sensor 440 and an increased positive signal is generated by the differential amplifier circuit and peak detector 412, the output from comparator 414 will be at ground. Conversely, during exhalation, the output of comparator 414 will be above ground.

The output of comparator 414 is also fed to an input point of one shot 418. When one shot 418 receives a positive signal from comparator 414 indicating an exhalation portion of a respiratory cycle, it produces a signal at ground which is input to the signal generator and alarm circuits. Upon receipt of a ground signal from comparator 414, indicating the inhalation portion of a respiratory cycle, one shot 418 produces a positive signal for a predetermined fixed period of time to the signal generator and alarm circuits. Signals from one shot 418 pass through diode 430 which, together with diode 431, isolates signals produced by one shot 418 from signals which may be generated by the alarm circuit, as discussed below.

Those familiar with the art will recognize that the sensor valve signal generator and oxygen valve signal generator circuits of the exemplary embodiment include analog circuit portions which provide the sensor-connection-delay interval and the supplemental-gas-administration delay interval, respectively. It may be seen that the arrangement of diode 434 in the analog timer portion of the sensor valve signal generator circuit will result in a positive signal generated by one shot 418 in response to inhalation flowing through the diode 434 rather that the resistance-capacitance portion of that circuit to immediately cause comparator 436 to generate a positive signal to cause gate 435 to energize coil 437 to place the sensor valve in the second mode to disconnect the sensor from the cannula hose and communicate the sensor with the ambient atmosphere. The arrangement of diode 438 in the gas valve signal generator circuit will cause a positive signal generated by the one shot 418 to pass through the resistance capacitance portion of the sensor valve signal generator circuit delaying the signal rise at the input point of comparator 442 for a period corresponding to the supplemental-gas-administration-delay period. Only after the delay period, when positive input reaches comparator 442, comparator 442 generates a ground signal to open gate 439 and de-energize coil 443 to place the gas valve in the second position in communication with the cannula hose. Conversely, when one shot 418 initiates a signal at ground, during an exhalation portion of a respiratory cycle, current may flow away from comparator 442 through the diode 438 to immediately signal comparator 442 to generate a positive signal to cause gate 439 to energize coil 443 causing the gas valve to switch to the first position, while current flowing away from comparator of the sensor valve signal generator must pass through the resistance capacitance portion of the circuit resulting in a time delay before the input to comparator 436 is at ground and the sensor valve is de-energized to switch from the second to the first mode again placing the sensor in communication with the cannula hose.

Those familiar with the art will also recognize that the placement of resistors 444 in the power circuits for the gas and sensor valves of the exemplary embodiment allows rapid response of the poppet valves when they are energized while conserving energy during the time intervals over which the valves are maintained in an energized state. When the valve circuits are initially energized, full voltage of, for example, six volts, is applied during the period in which the valve changes mode. However, after a period during which a charge on the capacitive portion of the circuit is reduced, current to the energized valve must flow through the resistive portion of the circuit resulting in a lower voltage being applied to the valve solenoid coil reducing power dissipation in the circuit while the valve remains in the power-on condition. If, for example, Resistors 445 are of 33 ohms, power savings of approximately 40% may be achieved during periods in which the valve is held in the energized mode.

Each time one shot 418 of the preferred embodiment produces a positive signal during the inhalation portion of the in vivo respiratory cycle, light emitting diode 424 is caused to light signaling the oxygen administration interval. Those familiar with the art will recognize that a period chosen as characteristic of an apneic event to activate the alarm can be set by adjustment of pot 426. Should the period between respiratory cycles exceed the set apneic event characteristic interval, for example, 30 seconds, the alarm timer circuit produces a positive output to cause latch 428 to latch up. The positive signal generated by latch 428 will then activate alarm 432, for example an acoustic alarm, on a continuing basis, and pass through diode 431 to the valve signal generators to initiate a continuing administration of supplemental gas to the in vivo respiratory system.

While an exemplary supplemental respiratory gas supply apparatus embodying the present invention has been shown, it will be understood, of course, that the invention is not limited to that embodiment. Modification may be made by those skilled in the art, particularly in light of the foregoing teachings. For example, digital timing devices might be used to control the respiratory gas administration cycle of the supplemental respiratory gas supply system rather than the analogue circuits of the exemplary embodiment and the system might provide that supplemetal gas be withheld at selected intervals for purposes of weaning the in vivo system from dependency upon the supplemental respiratory gas. It is, therefore, contemplated by the appended claims to cover any such modification which incorporates the essential features of this invention or encompasses the true spirit and scope of the invention.

I claim:

1. A method for supplying supplemental respiratory gas through a single hose cannula to an in vivo respiratory system, comprising the steps of:
   A. connecting a means for sensing pressure to the cannula hose to measure pressure within the cannula hose;
   B. monitoring the pressure within the cannula hose until a time, $t_O$, of an initial occurrence of a pressure less than atmospheric pressure;
   C. continuing to monitor the pressure for a predetermined period of time, $\Delta t_c$, until a time $t_1$;
   D. determining the magnitude of a pressure, $P_1$, occurring within the cannula hose during the period of time $\Delta t_c$;
   E. at time $t_1$, disconnecting the pressure sensing means for the cannula hose;
   F. waiting a predetermined period of time $\Delta t_1$, until a time $t_1'$;
   G. at time $t_1'$, connecting a source of supplemental gas to the cannula hose to begin a supplemental gas administration interval of providing supplemental gas to the in vivo respiratory system;
   H. continuing to provide supplemental gas to the in vivo system for a time interval $\Delta t_{sup}$, based upon the value $P_1$, in accordance with a predetermined relation, until a time $t_2$;
   I. at time $t_2$, disconnecting the source of supplemental gas from the cannula hose to end the supplemental gas administration interval;
   J. waiting a predetermined period of time $\Delta t_2$ until a time $t_2'$;
   K. at a time $t_2'$, reconnecting the pressure sensing means to the cannula hose to again monitor the pressure within the cannula hose; and,
   L. successively repeating steps A through K a plurality of times to provide supplemental gas to the in vivo respiratory system on a continuing basis.

2. A method for supplying supplemental gas to an in vivo respiratory system as in claim 1, comprising an additional first step of:
   calibrating the pressure sensing means at ambient atmospheric pressure.

3. A method for supplying supplemental gas to an in vivo respiratory system as in claim 1 further comprising the steps of:
   starting a timer device immediately upon performance of a step selected from among the steps A through K, to determine a time of expiration of an apneic event characteristic period after performance of the selected step; and
   at said time of expiration of the apneic event characteristic period, but only if the performance of the selected step has not reoccurred, activating an aepnic event alarm.

4. A method for supplying supplemental gas to an in vivo respiratory system as in claim 3, in which said apneic event alarm is an acoustic alarm.

5. A method of supplying supplemental gas to an in vivo respiratory system as in claim 3, in which said apneic event alarm is an optical alarm.

6. A method of supplying supplemental gas to an in vivo respiratory system as in claim 3, in which, beginning at the time of activation of the apneic event alarm, supplemental gas is provided continuously to the in vivo respiratory system.

7. A method for supplying supplemental gas to an in vivo respiratory system as in claim 1, in which the time interval $\Delta t_{sup}$ of the step of continuing to provide supplemental gas to the in vivo system for the time interval $\Delta t_{sup}$, is determined as a direct proportion of the pressure $P_1$ from an arithmetic formula of the form $\Delta t_{sup} = \alpha P_1$, where $\alpha$ is an arithmetic constant.

8. A method for supplying supplemental respiratory gas through a single hose cannula as in claim 1 in which the pressure, $P_1$, determined in step D is an instant pressure at time $t_1$.

9. A method for supplying supplemental respiratory gas through a single hose cannula as in claim 1 in chich the pressure, $P_1$, determined in step D is the most negative pressure occurring during the time $\Delta t_c$.

10. A mehtod for supplying supplemental respiratory gas through a single hose cannula to an in vivo respiratory system, comprising the steps of:
   A. connecting a means for sensing pressure to the cannula hose to measure pressure within the cannula hose;
   B. monitoring the pressure within the cannula hose until a time, $t_0$, of an initial occurrence of a pressure less than atmospheric pressure;
   C. determining the rate of change of pressure at the time $t_O$;
   D. at a time $t_1$, not prior to time $t_O$, disconnecting the pressure sensing device from the cannula hose;
   E. waiting a predetermined period of time $\Delta t_1$, until a time $t_1'$;
   F. at time $t_1'$, connecting a source of supplental gas to the cannula hose to begin a supplemental gas administration interval of providing supplemental gas to the in vivo respiratory system;
   G. continuing to provide supplemental gas to the in vivo system for a time interval $\Delta t_{sup}$, based upon the rate of change of pressure determined in step C, in accordance with a predetermined relation, until a time $t_2$;
   H. at time $t_2$, disconnecting the source of supplemental gas from the cannula hose to end the supplemental gas administration interval;
   I. waiting a predetermined period of time $\Delta t_2$ after time $t_2$, until a time $t_2'$;

J. at time $t_2'$, reconnecting the pressure sensing means to the cannula hose to again monitor the pressure within the cannula hose; and, K. successively repeating steps A through J a plurality of times to provide supplemental gas to the in vivo respiratory system on a continuing basis.

11. A method for supplying supplemental respiratory gas through a single hose cannula to an in vivo respiratory system, comprising the steps of:

A. connecting a means for sensing pressure to the cannula hose to measure pressure within the cannula hose;

B. monitoring the pressure within the cannula hose until a time, $t_O$, of an initial occurrence of a pressure less than atmospheric pressure;

C. waiting a predetermined period of time, $\Delta t_c$, until a time $t_1$;

D. determining the magnitude of a pressure, $P_1$, occuring within the cannula hose during the time $\Delta t_c$;

E. at time $t_1$, disconnecting the pressure sensing means from the cannula hose;

F. at a time $t'_1$, not prior to time $t_1$, connecting a source of supplemental gas to the cannula hose to begin a supplemental gas administration interval of providing supplemental gas to the in vivo respiratory system;

G. continuing to provide supplemental gas to the in vivo system for a time interval $\Delta t_{sup}$, based upon the value $P_1$ in accordance with a predetermined relation, until a time $t_2$;

H. at time $t_2$, disconnecting the source of supplemental gas from the cannula hose to end the supplemental gas administration interval;

I. at time $t_2'$, reconnecting the pressure sensing means to the cannula hose to again monitor the pressure within the cannula hose; and, J. successively repeating steps A through I a plurality of times to provide supplemental gas to the in vivo respiratory system on a continuing basis.

12. A method for supplying supplemental respiratory gas through a single hose cannula to an in vivo respiratory system, comprising the steps of:

A. connecting a means for sensing pressure to the cannula hose to measure pressure within the cannula hose;

B. monitoring the pressure within the cannula hose until a time, $t_O$, of an initial occurrence of a pressure less than atmospheric pressure;

C. waiting a predetermined period of time, $\Delta t_c$, after time $t_O$, until a time $t_1$;

D. determining the magnitude of a pressure, $P_1$, occurring within the cannula hose during the time $\Delta t_c$;

E. at time $t_1$, disconnecting the pressure sensing device from the cannula hose;

F. at time $t_1'$, connecting a source of supplemental gas to the cannula hose to begin a supplemental gas administration interval of providing supplemental gas to the in vivo respiratory system;

G. continuing to provide supplemental gas to the in vivo system for a time interval $\Delta t_{sup}$, based upon the value $P_1$ in accordance with a predetermined relation, after $t_1'$, until a time $t_2$;

H. at time $t_2$, disconnecting the source of supplemental gas from the cannula hose to end the supplemental gas administration interval;

I. at a time $t'_2$; not prior to time $t_2$, reconnecting the pressure sensor device to the cannula hose to again continuously monitor the pressure within the cannula hose; and, J. sucessively repeating steps A through I a plurality of times to provide supplemental gas to the in vivo respiratory system on a continuing basis.

13. A method for controlling the supply of a supplemental respiratory gas through a single hose cannula to an in vivo respiratory system, comprising the steps of:

A. connecting a means for sensing pressure to the cannula hose to measure pressure within the cannula hose;

B. monitoring the pressure within the canula hose until a time, $t_0$, of an initial occurrence of a pressure less than atmospheric pressure;

C. at time $t_1$, not prior to $t_0$, disconnecting the pressure sensing device from the cannula hose;

D. at a time $t_1'$, not prior to $t_1$, connecting a source of supplemental gas to the cannula hose to begin a supplemental gas administration interval of providing supplemental gas to the in vivo respiratory system;

E. continuing to provide supplemental gas to the in vivo system for a time interval $\Delta t_{sup}$, until a time $t_2$;

at time $t_2$, disconnecting the source of supplemental gas from the cannula hose to end the supplemental gas administration interval;

H. waiting a predetermined period of time $\Delta t_2$, until a time $t_2'$;

I. successively repeating the steps A through H a plurality of times to provide supplemental gas to the in vivo system on a continuing basis.

14. An apparatus for supplying supplemental respiratory gas from a gas source through a single hose cannula to an in vivo respiratory system during successive respiratory cycles, each cycle beginning with a respiratory demand by the in vivo respiratory system characterized by a negative pressure occurrence at an interface between the cannula hose and the in vivo system, comprising:

means for sensing pressure and generating a pressure indicative signal representative of the magnitude of the pressure sensed;

alternative communication means responsive to first control signals to switch between two alternative modes, a first mode communicating said pressure sensing means with the cannula hose so that a pressure with in the hose can be monitored and a second mode communicating said pressure sensing means with ambient atmospheric pressure;

means for connecting the apparatus to a source of supplemental gas;

valve means responsive to second control signals to switch between two alternative positions, said valve means isolating the source of supplemental gas from the cannula hose when in the first position and allowing supplemental gas from the source to flow into the cannula hose when in the second position;

control means, including timing means, for receiving said pressure indicative signal and selectively generating said first and second control signals, said control means responsive to initiation of operation of the apparatus to generate said first control signal to place said alternative communication means in said first mode and said second control signal to place said valve means in said first position to cause said pressure sensing means to sense a pressure within the cannula hose, said control means thereafter receiving said pressure indicative signal and generating said first and second control signals in accordance with said pressure indicative signal, said control means responsive to initial reception of a pressure indicative signal indicative of a pressure less than atmospheric pressure, at a time $t_0$, to initiate a sequential, supplemental-gas-administration cycle by generating a firt control signal at a time $t_1$, a predetermined time interval $\Delta t_c$ after time $t_O$, to switch said alternative communication means to its second mode; generating a second control signal at a time $t_1'$, a predetermined time interval $\Delta t_1$ after time $t_1$, to switch said valve means from said first position to said second position to begin an interval of supplemental respiratory gas administration; generating said second control signal at a time $t_2$, a time interval $\Delta t_{sup}$ after time $t_1'$, to switch said valve means from the second position to the first position to end the interval of supplemental gas administration and thereby define a period of supplemental gas administration, $\Delta t_{sup}$; generating a first control signal, at a time $t_2'$, a predetermined time interval $\Delta t_2$ after time $t_2$, to switch said alternative communication means to its first mode to communicate the pressure sensing means with the cannula hose and allow said pressure sensing means to generate a pressure indicative signal indicative of the pressure within the cannula hose; said control unit thereafter responsive to said pressure indicative signal to initiate continuing, successive, supplemental-gas-administration cycles in response to demand by the in vivo respiratory system.

15. A supplemental respiratory gas supply apparatus as in claim 14 further comprising:
means for calibrating said control means at ambient atmospheric pressure.

16. A supplemental respiratory gas supply apparatus as in claim 14 in which the supplemental-gas-administration interval, $\Delta t_{sup}$, defined by said sequential cycle of said control means is a predetermined constant time period.

17. A supplemental respiratory gas supply apparatus as in claim 14 in which the supplemental gas administration interval, $\Delta t_{sup}$, defined by said sequential of said control means is a time period determined as a function of the most negative pressure magnitude occurring during time interval $\Delta t_c$.

18. A supplemental respiratory gas supply apparatus as in claim 14 in which the supplemental gas administration interval, $\Delta t_{sup}$, defined by said sequential of said control means is a time period determined as a function of the rate of change of pressure with time at the time of the initial reception of a pressure indicative signal indicative of a pressure lower than atmospheric pressure, $t_O$.

19. A supplemental respiratory gas supply apparatus as in claim 14 in which the time interval $\Delta t_c$ is determined by electrical impedance and mechanical inertia of the supplemental respiratory gas supply apparatus, including the control means.

20. A supplemental respiratory gas supply apparatus as in claim 14 in which the supplemental-gas-administration interval, $\Delta t_{sup}$, defined by said sequential cycle of said control means, is a time period determined as a function of a pressure, $P_1$, indicated by the pressure sensor at the time, $t_1$, that said alternative communication means is switched to its second mode.

21. A supplemental respiratory gas supply apparatus as in claim 20, in which the supplemental-gas-administration interval defined by said sequential cycle of said control device, $\Delta t_{sup}$, is directly proportional to the amount by which the pressure, $P_1$, indicated by the pressure sensing means at the time said alternative communication means is switched to its second mode, $t_1$, is below atmospheric pressure.

22. An apparatus for supplying supplemental respiratory gas as in claim 14 in which said valve means is in the first position when in repose in a power off condition so that, in the event of a power failure, supplemental respiratory gas is continuously provided to the in vivo respiratory system.

23. An apparatus for supplying supplemental respiratory gas through a single hose cannula to an in vivo respiratory system comprising:
means for sensing pressure and generating a pressure indicative signal representative of the magnitude of the pressure sensed;
means for providing alternative fluid communication, said alternative communication means having two modes, a first mode in which said alternative communication means provides fluid communication between said pressure sensing means and an interior portion of the cannula hose so that said pressure sensing means senses a pressure in the portion of the cannula hose and generates a pressure signal indicative thereof, and a second mode in said alternative communication means provides fluid communication between said pressure sensing means and an ambient atmosphere so that said pressure sensing means generates a pressure indicative signal indicative of ambient atmospheric pressure, said alternative communication means responsive to a first and second control signal to switch to the first and second mode, respectively;
means for controlling a flow of supplemental gas, said gas flow control means in fluid communication with a source of supplemental respiratory gas and having two positions, a first position in which said flow control means isolates the supplemental gas source from the cannula hose and a second position in which said gas flow control means provides fluid communication between the gas source and the cannula hose so that supplemental respiratory gas flows into the cannula hose, said gas flow control means responsive to a third and fourth control signal to switch to the first and second position, respectively;
means for receiving said pressure indicative signal, determining when said pressure indicative signal is indicative of a negative pressure less than atmospheric pressure, and, upon receiving such a negative pressure indicative signal, generating a cycle signal continuously until its termination at the end of a cycle time interval;
means for controlling the mode of said flow control means in response to said cycle signal, said mode control means operative to receive said cycle signal and generate said third and fourth control signals in such a manner as to switch said flow control means in the second position and maintain said flow control means in said second position continuously from a time said cycle signal is initially generated until a gas disconnect time following the time of initial generation of said cycle signal by a predetermined gas-connect-delay interval, switching said flow control means from said first position to said second position at said gas connect time and maintaining said flow control means in said second position continuously while said cycle signal continues to be generated over a remainder of the cycle time interval, and upon the termination of said cycle signal, switching said flow control means from the second position to the first position and maintain said flow control means in the second position until said cycle signal is again generated; and means for controlling the mode of said alternative communication means in response to said cycle signal, said mode control means operative to receive said cycle signal and to generate said first and second control signals in such a manner as to switch said alternative communication means from the first mode to the second mode immediately upon generation of said cycle signal and to continuously maintain said alternative communication means in said second position while said cycle signal is generated over the cycle time interval and for an additional predetermined fixed sensor-connect-delay interval, and thereafter switching said alternative communication means to the first mode and maintaining said flow control means in the first mode continuously until the cycle signal is again generated.

24. An apparatus for supplying supplemental respiratory gas through a single hose cannula as in claim 23 in which said cycle signal is of a duration which is a multiple of a pre-determined incremental time period.

25. An apparatus for supplying supplemental gas, as in claim 23 in which said cycle signaling means comprises:
means for retaining a negative peak in said pressure indicative signals, said peak retaining means interposed between said pressure sensing means and said comparing and signaling means and operative to receive said pressure indicative signal and to produce a modified pressure indicative signal, said modified pressure indicative signal indicative of a pressure identical to the pressure indicated by said pressure indicative signal of said pressure sensing means except beginning at a time when the rate of pressure increase indicated by said pressure indicative signal exceeds a predetermined rate of increase, said modified pressure indicative signal indicating a pressure increasing at a constant predetermined rate of pressure increase equal to said predetermined rate beginning at said time of excess rate increase until a time said modified pressure indicative signal is again indicative of a pressure identical to the pressure indicated by said pressure indicative signal, said modified pressure signal thence remaining identical to the pressure indicated by said pressure indicative signal until a pressure increase indicated by said pressure indicative signal again exceeds the predetermined rate of increase; and means for comparing and signaling, adapted to receive both said modified pressure indicative signal and a calibrated atmospheric pressure indicative signal and compare said pressure indicative signal to said calibrated atmospheric pressure indicative signal and to generate a cycle signal when said pressure indicative signal is indicative of a pressure less than atmospheric pressure.

26. An apparatus for supplying supplemental respiratory gas as in claim 25 in which said supplemental respiratory gas control means is in the second position when in repose in a power off condition so that, in an ocurrence of power failure, supplemental respiratory gas is continuously provided to the in vivo respiratory system.

27. An apparatus for supplying supplemental respiratory gas as in claim 25 in which said alternative communication means and said supplemental gas control means each comprise a poppet valve.

28. An apparatus for supplying supplemental gas, as in claim 25 in which said cycle signal is of a duration which is a multiple of a pre-determined incremental time period.

29. An apparatus for supplying supplemental respiratory gas as in claim 25 further comprising:
means for switching said alternative communication means to the second mode when power is first supplied to the apparatus;
latch means to produce a first latch signal when power is first supplied to the apparatus and to produce a second latch signal upon generation of a cycle signal; and,
ramp signal generating means operative to receive said latch signals and, in response to said first latch signal, to generate a trial calibration atmospheric pressure indicative signal beginning at a pressure indicative value higher than a predetermined atmospheric pressure indicative value and indicative of a pressure decreasing at a constant rate over time until receiving said second latch signal and thereafter to generate a constant calibrated atmospheric pressure indicative signal until the power is cut off.

30. An apparatus for supplying of a supplemental respiratory gas through a single hose cannula to an in vivo respiratory system as in claim 23 in which said cycle time interval is determined based upon a momentary rate of change of the pressure signal at the time of said negative pressure indication.

31. In a supplemental respiratory gas supply apparatus for providing supplemental respiratory gas to an invivo respiratory system through a cannula hose in response to demands of the invivo system, the system having a pressure sensor, a source of supplemental respiratory gas at a pressure greater than atmospheric pressure and control means, said control means operational to connect and disconnect said sensor to the cannula hose at a point of sensor communication to monitor pressure within the hose and to connect and disconnect said gas source to said cannula hose to introduce supplemental gas into the hose during periods of supplemental gas administration, the improvement comprising:
said control means disconnecting said sensor from said cannula hose during the periods of supplemental gas administration and including means for maintaining said sensor disconnected from said hose during a predetermined sensor-connect-delay interval after disconnecting said source from said hose thereby allowing pressure gradients within the hose resulting from the introduction of respiratory gas into the hose to reduce sufficiently to assure pressure at the point of sensor communication is not sufficient to damage or aggravate drift of the sensor before connecting said sensor to said hose to monitor pressure within the hose.

32. In a supplemental respiratory gas supply apparatus for providing supplemental respiratory gas to an in vivo respiratory system through a cannula hose in response to demands of the in vivo system characterized by an occurrence of negative pressure at a point of interface between the cannula hose and the in vivo system, the system having a means for sensing pressure within the cannula hose, a source of supplemental respiratory gas and a control means, said control means operational to connect said gas source to the cannula hose to introduce supplemental gas into the hose over periods of supplemental gas supply intervals and to disconnect said source from said hose to end the duration of supply intervals, a method of control comprising the steps of;

monitoring the pressure within the cannula hose to detect an initial occurrence of negative pressure;

determining the largest magnitude of negative pressure occurring over a sample period following said initial occurrence of negative pressure; and thereafter introducing supplemental gas into the hose for a supply interval of a duration determined by said largest magnitude of negative pressure.

33. A method for controlling a supplemental respiratory gas supply apparatus for providing supplemental respiratory gas to an in vivo respiratory system through a cannula hose in response to demands of the in vivo system characterized by an occurrence of negative pressure at a point of interface between the cannula hose and the in vivo system, the system having a means for sensing pressure within the cannula hsoe, a source of supplemental respiratory gas and a control means, said control means operational to connect said gas source to the cannula hose, to introduce supplemental gas into the hose over periods of supplemental gas supply intervals and to disconnect said source from said hose to end the duration of supply intervals, comprising the steps of;

monitoring the pressure within the cannula hose to detect an initial occurrence of negative pressure;

determining the rate of change of pressure at the time of said initial occurrence; and, thereafter introducing supplemental gas into the hose for a supply interval of a duration determined by said rate of charge of pressure.

34. A method for controlling a supplemental respiratory gas supply apparatus for providing supplemental respiratory gas to an in vivo respiratory system through a cannula hose in response to demands of the in vivo system characterized by an occurrence of negative pressure at a point of interface between the cannula hose and the in vivo system, the system having a means for sensing pressure within the cannula hose, a source of supplemental respiratory gas and a control means, said control means operational to connect said gas source to the cannula hose to introduce supplemental gas into the hose over periods of supplemental gas supply intervals and to disconnect said source from said hose to end the duration of supply intervals, comprising the steps of;

monitoring the pressure within the cannula hose to detect an initial occurrence of negative pressure;

determining the magnitude of an instant pressure occurring within the hose at a predetermined time after said initial occurrence; and thereafter introducing supplemental gas into the hose for a supply interval which is determined by the magnitude of said pressure.

* * * * *